United States Patent
Minick et al.

[11] Patent Number: 5,700,257
[45] Date of Patent: Dec. 23, 1997

[54] AMBULATORY IV PUMP TRANSPORT APPARATUS

[75] Inventors: Steven E. Minick, San Diego; Judith A. Segerson, La Jolla; William C. Rednour, San Diego, all of Calif.

[73] Assignee: Abbott Laboratories, Abbott Park, Ill.

[21] Appl. No.: 574,672

[22] Filed: Dec. 19, 1995

[51] Int. Cl.$^6$ ................................................. A61B 19/00
[52] U.S. Cl. .......................... 604/408; 604/403; 604/345
[58] Field of Search ........................... 604/93, 113, 174, 604/262, 263, 327, 345, 403, 408

[56] References Cited

U.S. PATENT DOCUMENTS

| | | | |
|---|---|---|---|
| 4,561,576 | 12/1985 | Lowe et al. | 224/209 |
| 4,804,367 | 2/1989 | Smith et al. | 604/408 |
| 5,279,589 | 1/1994 | Feldman | 604/408 |
| 5,295,964 | 3/1994 | Gauthier | 604/408 |
| 5,348,539 | 9/1994 | Herskowitz | 604/141 |

Primary Examiner—John G. Weiss
Assistant Examiner—Ki Yong O
Attorney, Agent, or Firm—Neal D. Marcus; Ronald M. Anderson

[57] ABSTRACT

A pack (10) for carrying an IV bag (12) and an ambulatory IV pump (16). The pack includes an inner back (30) and an outer back (32) that are sewn together on three edges to form a pocket (38) in which a plastic plate (40) is inserted to provided rigidity. A pair of inner flaps (64, 66) secure the IV bag against the back of the pack. Several straps (42, 50, 52, 62) also secure the IV bag in place, limiting its lateral and longitudinal movement relative to the back of the pack. Outer flaps (70, 72) overlap to enclose the IV bag. One of the outer flaps includes a pocket (14) in which the IV pump (16) is carried. The flaps and straps are secured by engaging a hook material attached to one surface of the strap or flap to a loop material attached to another surface. Although the pack can be carried in a variety of different sizes and styles of carrying bag, an exemplary carrying bag (110) is disclosed that is ideally suited for safely transporting the pack while a medicinal fluid is infused into the body of a patient.

20 Claims, 5 Drawing Sheets

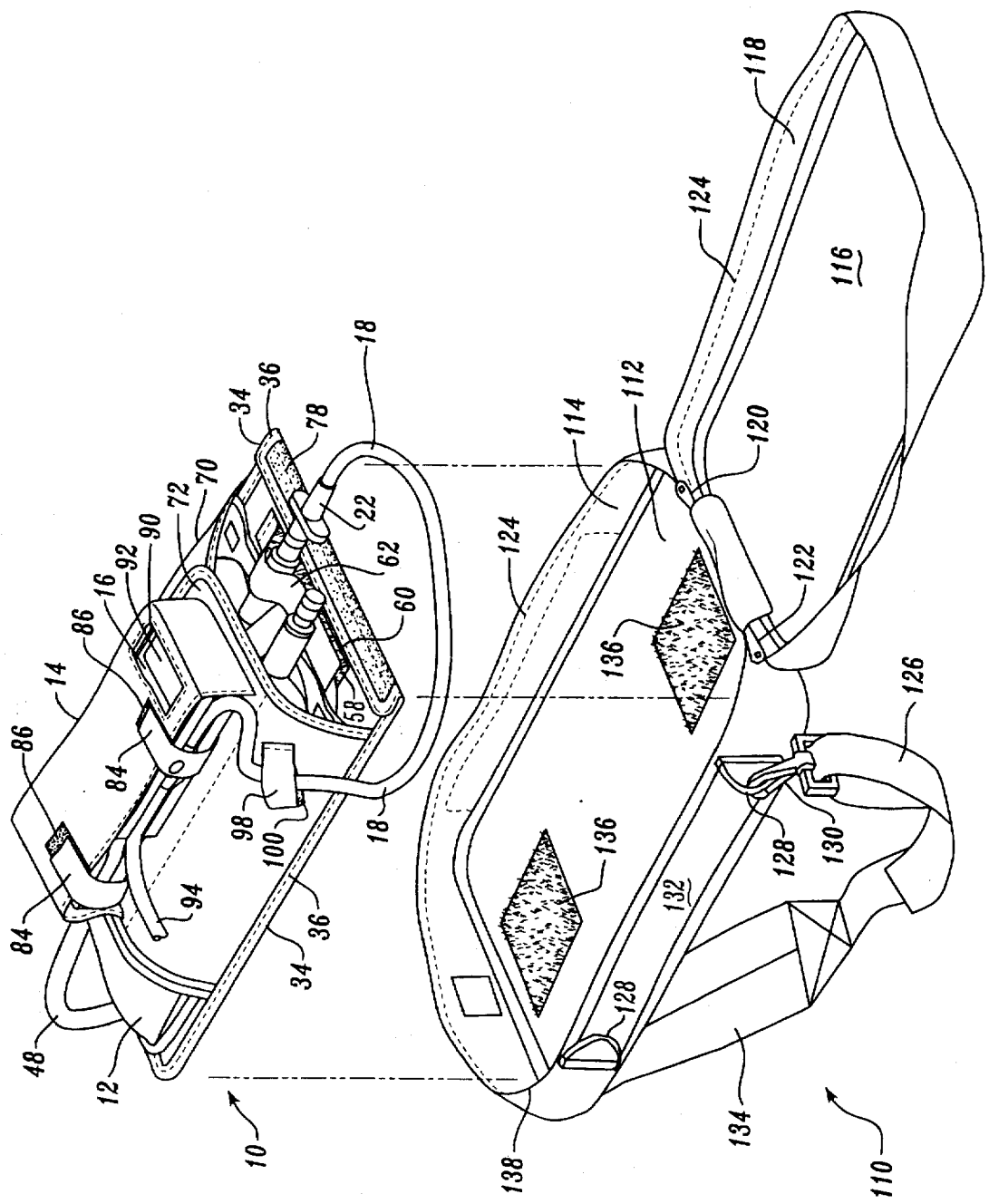

AMBULATORY IV PUMP TRANSPORT APPARATUS

FIELD OF THE INVENTION

The present invention generally relates to apparatus for transport of a medical device, and more specifically, to apparatus for transport of an intravenous (IV) pump by a patient while a medicinal fluid is infused into the patient's body.

BACKGROUND OF THE INVENTION

Various types of medication are preferably infused into a patient's body over an extended period of time. For those undergoing such treatment, there may be little justification to remain bedridden and inactive while the medication is being infused. Modern IV pumps that are controlled by microprocessors can be programmed to deliver a specific volume of medication, at a specified flow rate, over a defined time interval and can infuse the medication without attention from either the patient or medical personnel. These pumps are battery powered and are designed to be carried about by the patient while infusing the medicinal fluid into the patient's body, enabling the patient to enjoy a substantial freedom to move about and engage in normal daily activities.

Although most ambulatory IV pumps are relatively compact, the source of the medicinal fluid delivered by the pump is typically a somewhat larger container, such as a one liter IV bag. Since a patient may want to continue with normal daily activities and to be around other people while the medication is being infused, it is clearly preferable that the apparatus used for infusing the medication be as unobtrusive as possible. The ambulatory IV pump and the reservoir supplying the medicinal fluid are thus preferably hidden from view in a carrying pack supported by a shoulder strap or belt to enable the apparatus to be more efficiently carried by the patient.

Packs or bags that are specifically designed for carrying an ambulatory IV pump and IV bag are available from different manufacturers in a wide range of styles, colors, and fabrics. However, such carrying packs usually do not include straps or pockets that are able to accommodate various size IV pumps and medication reservoirs. Moreover, considerable variation exists in the shape and configuration of ambulatory IV pumps, so that a particular carrying bag preferred by a patient may not properly support the IV pump specified by a physician for use by that patient. If proper support for the pump and IV bag is not provided in the carrying bag selected by the patient, it is possible that damage to the pump may occur during transport or that fluid lines that extend between the IV bag and the pump or between the pump and the patient may become twisted or crimped, blocking the flow of medication to the patient.

Clearly, it would be preferable if an ambulatory IV pump could be safely transported in a carrying bag of the patient's choice without concern for damage to the pump and proper support for the IV bag and associated fluid lines. A patient could then safely select any preferred carrying bag of sufficient size to accommodate the IV pump and drug reservoir. Currently, the prior art does not provide any means to achieve this flexibility.

SUMMARY OF THE INVENTION

In accordance with the present invention, a pack is defined for transporting an ambulatory IV pump and an IV bag while a medicinal fluid in the IV bag is infused into a patient by the pump. The pack includes a pack board sized to support the IV bag, with one side of the IV bag in contact with the pack board. A plurality of flaps and a plurality of straps connected to the pack board are employed for securing the IV bag to the pack board, both laterally and transversely. A pouch is flexibly connected to the pack board and is sized to hold the ambulatory IV pump during transport.

The pack further comprises a hook material and a loop material that are disposed on the plurality of flaps and on the plurality of straps. An example of such material is sold under the trademark VELCRO™. The hook and loop materials are used for securing the IV bag to the pack board. The hook material engages the loop material to couple the plurality of flaps in overlapping closure and to hold the plurality of straps in place.

In the preferred form of the invention, the pack board comprises a pocket made of fabric. A plastic plate is inserted within the pocket to provide rigidity to the pack board.

The plurality of flaps include two inner flaps that are flexibly connected to the pack board to encompass a middle portion of the IV bag. The inner flaps are connected together where the inner flaps overlap to provide lateral support for the IV bag. In addition, the plurality of straps include a strap that is flexibly connected to the pack board adjacent one end. This strap overlaps the inner flaps and is connected to the inner flaps to restrain one end of the IV bag.

Furthermore, the plurality of straps include a strap that is flexibly connected to one end of the pack board and disposed so that the strap is adapted to pass through a hanger slot provided on an end of the IV bag. This strap then attaches to the pack board to secure the IV bag to the pack board.

Two outer flaps are flexibly connected to opposite sides of the pack board. The outer flaps overlap each other and substantially cover the IV bag when the flaps are folded over the bag. The pouch is disposed on an outer surface of the one of the outer flaps.

The pouch preferably includes an opening for insertion of the ambulatory IV pump. The plurality of straps include a strap for securing the ambulatory IV pump inside the pouch.

The plurality of straps also preferably include a strap that is connected to the pack board adjacent one end thereof. This strap extends generally parallel to that end of the pack board and is employed for securing an outlet port of the IV bag to the pack board.

A hanger loop is preferably disposed adjacent one end of the pack board. This hanger loop can be used to support the pack board while the medicinal fluid is being infused.

While not required, the invention may further comprise a carrying bag for enclosing and transporting the pack board, the plurality of flaps, the plurality of straps, the pouch, the IV bag secured on the pack board, and the ambulatory IV pump secured in the pouch. This carrying bag preferably includes a shoulder strap to facilitate transport of the bag with its contents.

Virtually any carrying bag of size sufficient to hold the pack board with the IV bag and pump secured therein can be used for transporting the ambulatory IV pump and IV bag on the pack board. The relatively rigid pack board supports the IV bag and the pump and the straps and flaps restrain these components so that they do not shift around inside the carrying bag. As a result, the ambulatory IV pump is protected from damage, and possible crimping of fluid lines connecting the IV bag to the pump and of fluid lines used for conveying the medicinal fluid to the patient is avoided.

BRIEF DESCRIPTION OF THE DRAWING FIGURES

The foregoing aspects and many of the attendant advantages of this invention will become more readily appreciated as the same becomes better understood by reference to the following detailed description, when taken in conjunction with the accompanying drawings, wherein:

FIG. 5 is an exploded view of the transport pack relative to an exemplary carrying bag, showing the transport pack securing the IV bag and ambulatory IV pump for transport being inserted into the carrying bag.

DESCRIPTION OF THE PREFERRED EMBODIMENT

Figure 2:
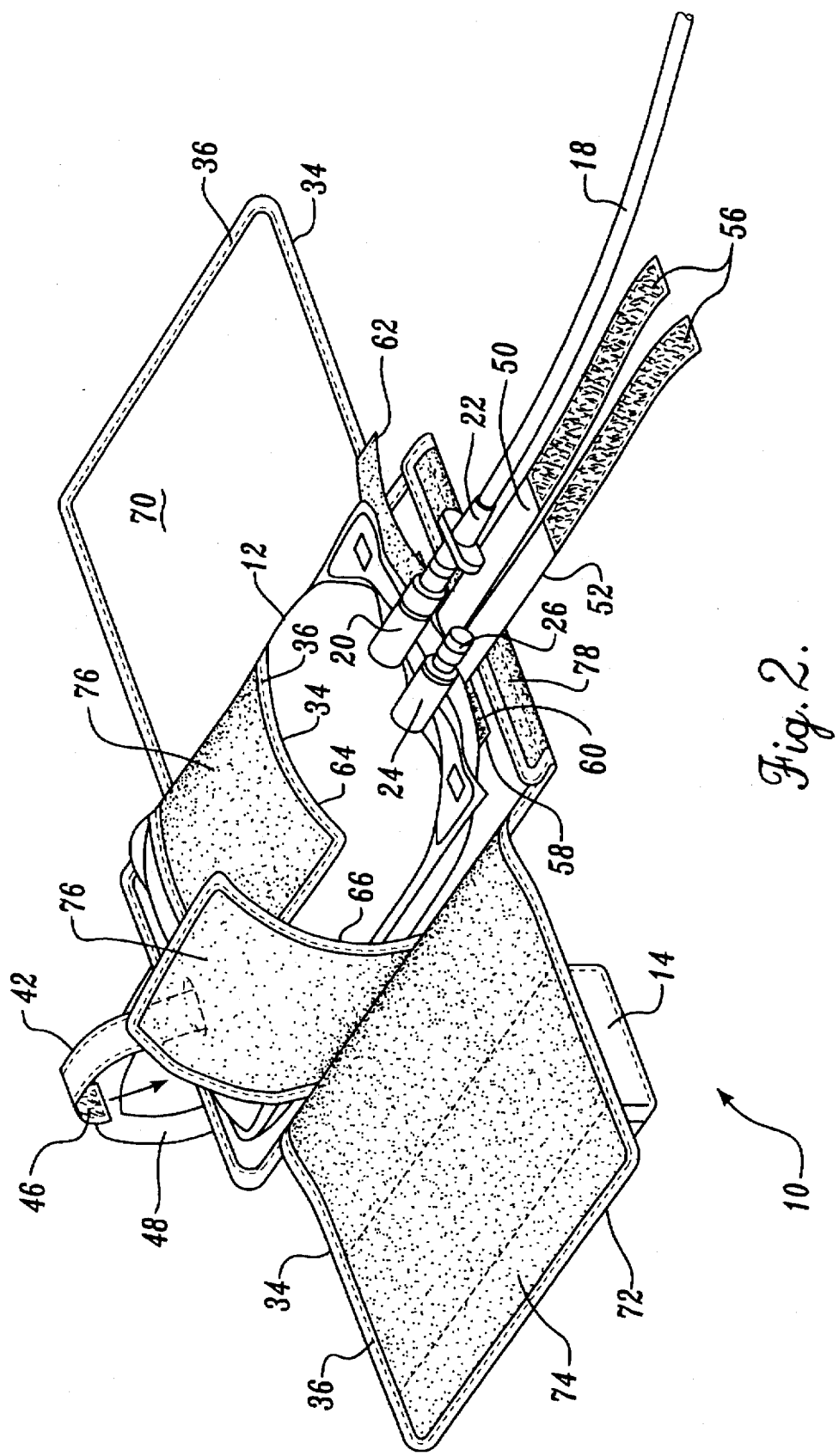
FIG. 2 is an isometric view of the IV bag and transport pack, showing the IV bag partially secured to the transport pack.
Figure 3:
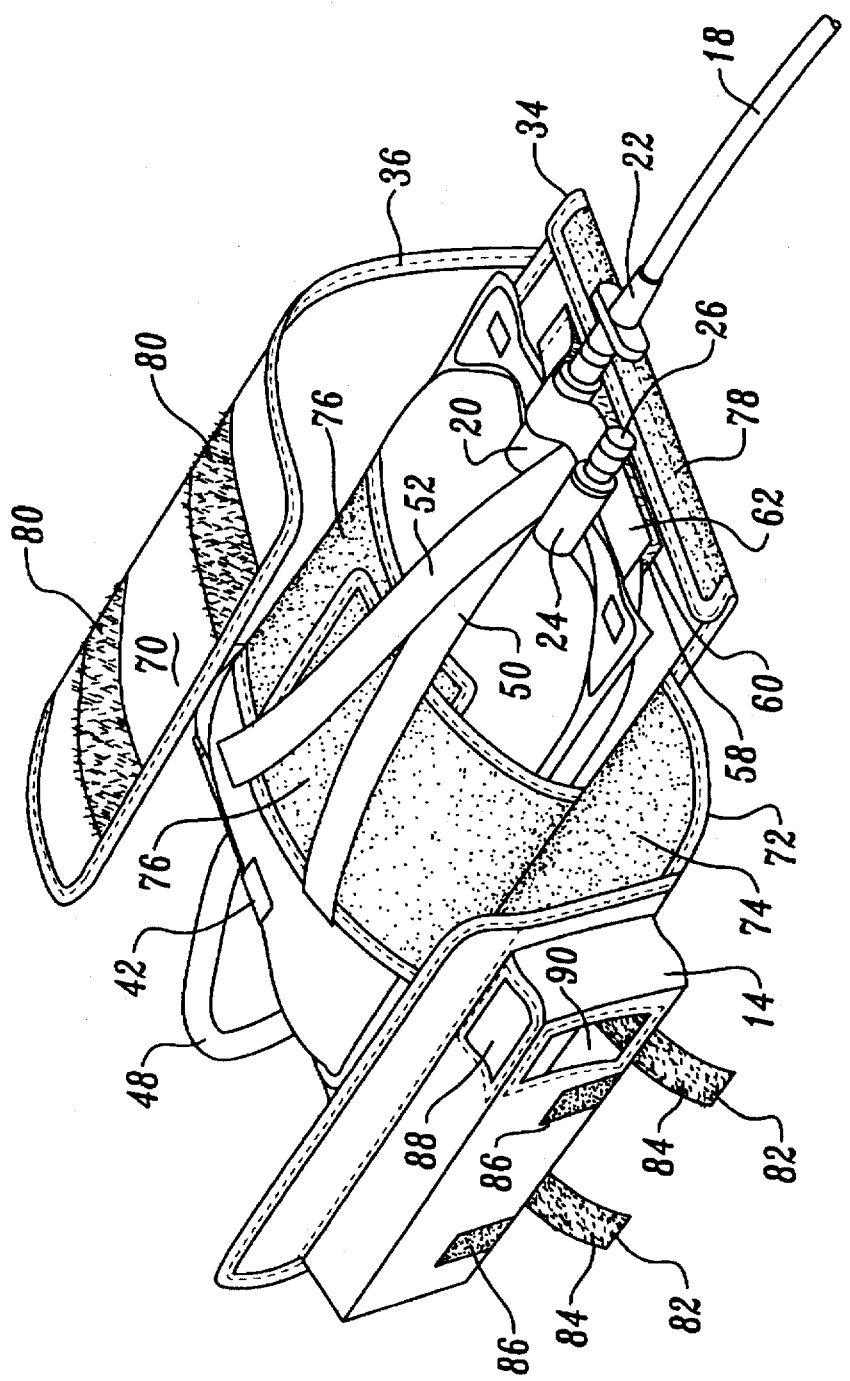
FIG. 3 is an isometric view of the IV bag and transport pack, showing the IV bag more fully secured to the transport pack.
Figure 4:
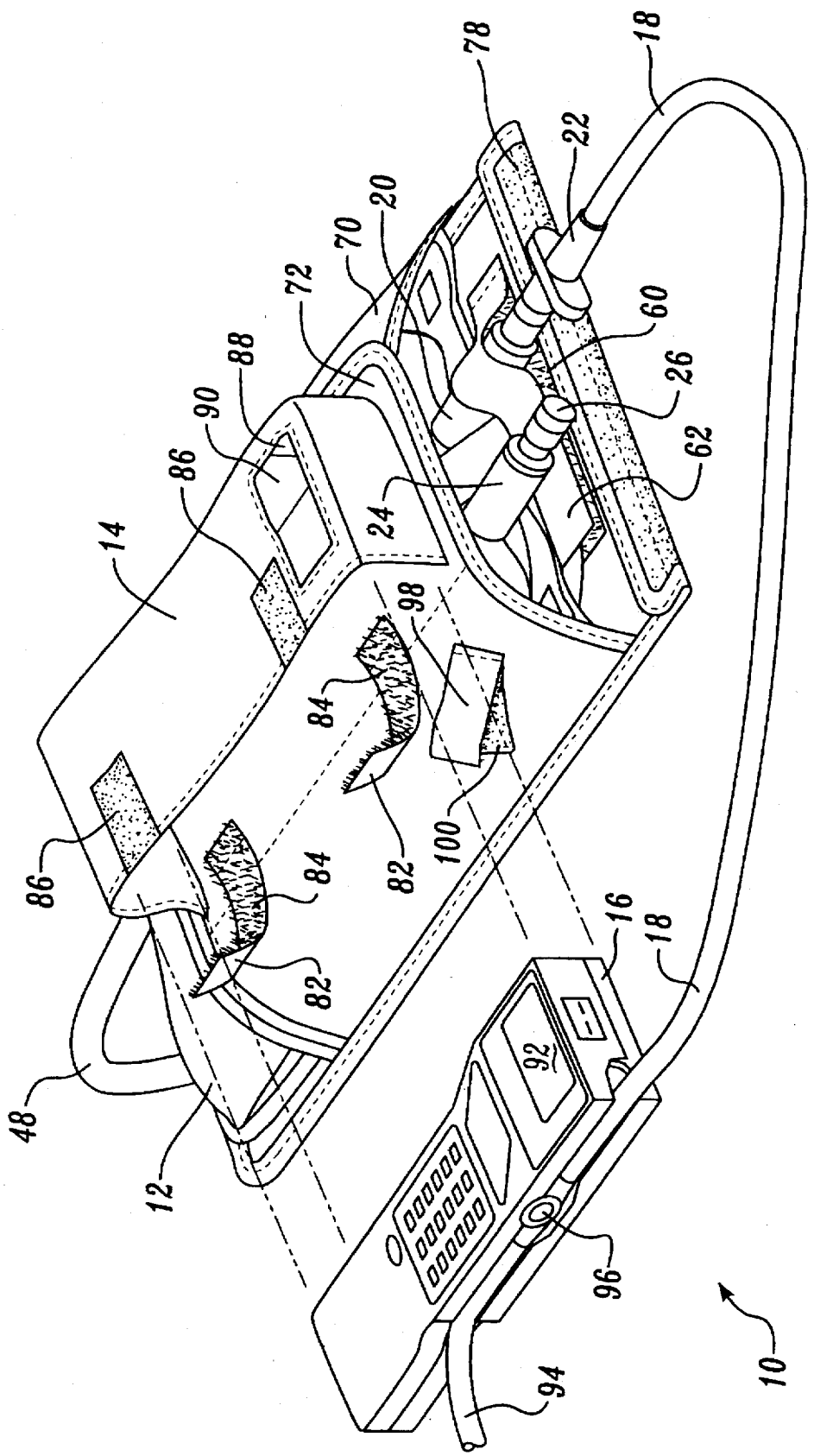
FIG. 4 is an exploded view of the ambulatory IV pump relative to the transport pack, showing the IV bag and transport pack assembly as the IV pump is inserted into a pouch.

FIGS. 1–4 illustrate a preferred embodiment for an ambulatory pump transport pack 10 for use in transporting an IV bag 12 and an ambulatory IV pump 16 (first shown in FIG. 4). These drawings illustrate the steps implemented to secure IV bag 12 inside pack 10 and IV pump 16 inside a pouch 14 on the pack. In the preferred embodiment, IV pump 16 comprises a rotary peristaltic pump. However, it is contemplated that the present invention could readily be adapted for use in transporting other types of ambulatory IV pumps. Similarly, the preferred embodiment of pack 10 is disclosed in connection with carrying a conventional IV bag 12. However, it is also contemplated that the present invention can readily be modified for carrying other types of medicinal fluid reservoirs having a different shape or configuration.

IV bag 12 supplies medicinal liquid that is stored within the bag to pump 16 through a supply line 18. Supply line 18 is coupled in fluid communication to the interior of IV bag 12 through a conventional bag spike connector 22 that is forced through an elastomeric seal (not shown) on an outlet port 20 at one end of the IV bag. Adjacent outlet port 20 is a secondary port 24, which is closed with a drug injection stopper 26 through which a drug may be injected into the medicinal fluid inside IV bag 12 using a syringe (not shown), as is generally well known to those of ordinary skill in the art.

Figure 1:
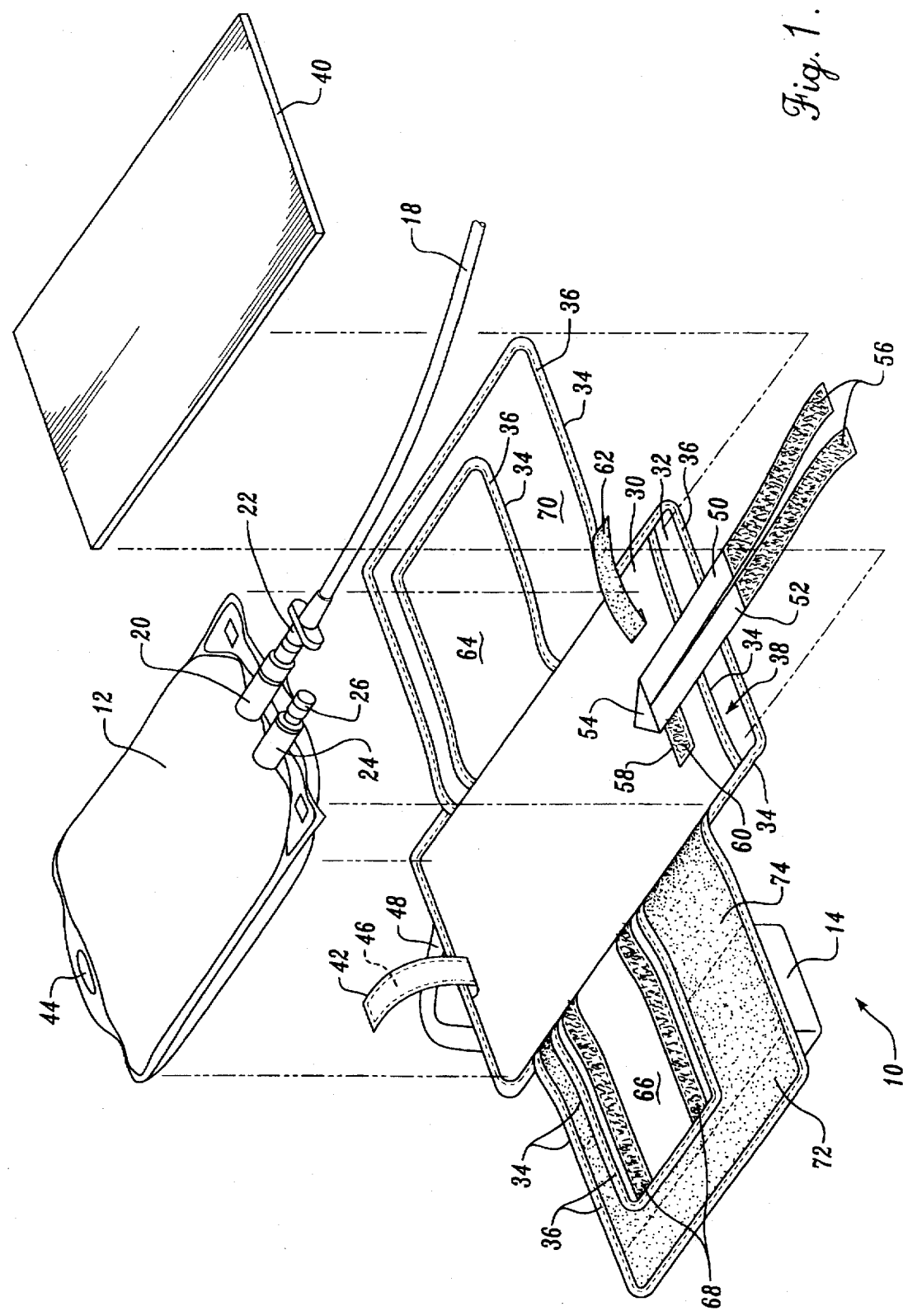
FIG. 1 is an exploded view showing a transport pack, and an IV bag that is to be carried in the transport pack.

As shown in FIG. 1, IV bag 12 is generally rectangular, being fabricated from two sheets of an elastomeric plastic material that are sealingly joined together around a peripheral seam. Pack 10 includes an inner back 30, against which the undersurface of IV bag 12 (as shown in FIG. 1) is placed, in a first step that is practiced in securing IV bag 12 inside pack 10. Inner back 30 is slightly wider and longer than IV bag 12 and is attached around three of its four edges to corresponding edges of an outer back 32. Outer back 32 is approximately the same width as inner back 30, but is about one inch longer, the additional length extending beyond the edge (at one end) of inner back 30 that is not attached to outer back 32.

Inner back 30 and outer back 32 thus define a pocket 38, which is open at the end of the inner back that is not connected to the outer back. A plastic plate 40 having a length and width substantially equal to the length and width of pocket 38 is inserted into the pocket through this open end. Plastic plate 40 provides stiffening for pack 10 to improve the support that it provides for IV bag 12.

The periphery of inner back 30 and outer back 32, as well as other flaps attached to the inner and outer back along opposite sides thereof are covered with a binding strip 34. The binding strip comprises woven nylon or other fabric that is folded around the edges of the inner and outer backs and flaps, and is attached by stitching through the material comprising these components with thread 36. Binding strip 34 protects the edges of these components of pack 10 against unraveling, and finishes the edges to improve the overall appearance of pack 10.

At about the midpoint of the end of inner back 30 opposite that at which pocket 38 is disposed, a strap 42 is sewn to the inner back so that the free end of the strap extends longitudinally along the center line of the inner back. Strap 42 is provided for securing one end of IV bag 12 to inner back 30 by passing the strap through an eye 44 that is formed in the peripheral flange of IV bag 12, at the end of the IV bag opposite that at which the outlet port is disposed. A strip of hook material 46 is attached to the one surface of strap 42. The hook material comprises one component of a plastic hook and fiber loop mechanism that is used extensively in pack 10 to secure straps and flaps in place. The hook and loop material is distributed under the trademark VELCRO™, as is well known to those in this art.

Although not shown in the FIGURES, the strip of hook material on strap 42 engages a corresponding patch of loop material on the back surface of outer back 36 after passing through eye 44, thereby securing the end of IV bag 12 in place on pack 10. A hanger strap 48 is formed with a strip of material that is attached to outer back 32 at the same end as strap 42, by stitching through the strip and outer back 32 with thread 36. Hanger strap 48 is intended for use in carrying pack 10 and can be used for hanging the pack with the IV bag and pump secured therein, while a medicinal fluid is administered to a patient.

At the opposite end of inner back 30 and outer back 32 from hanger strap 48 are disposed top straps 50 and 52. These two straps are constructed from a single strip of material that is folded back on itself, forming a "V-like" fold 54 that is attached to inner back 30 with stitches of thread 36. The V-like fold is attached at a point inset approximately two inches from the open end of inner back 30, along the longitudinal axis of the inner back. Approximately one half of one surface of top straps 50 and 52, near their tag ends, is covered with strips of hook material 56. Adjacent V-fold 54, a small patch of hook material 60 is attached to the inner back with stitches of thread 58. This patch of hook material is employed for securing a strip of loop material 62, after the strip has been passed over outlet port 20 on IV bag 12, as noted below.

Flexibly attached along one side of inner back 30 and outer back 32 is a first inner flap 64. Directly opposite, on the other side of inner back 30 is flexibly attached a second inner flap 66. The first and second inner flaps are sufficiently long so that they overlap each other when folded over IV bag 12. Parallel strips of hook material 68 are attached to the inner surface of second inner flap 66 for use in securing the second inner flap to the first inner flap, when these two flaps are folded over the top of IV bag 12, as shown in FIG. 2. The outer surfaces of both first inner flap 64 and second inner flap 66 are covered with loop material 76. Strips of hook material 68 on the second inner flap thus engage loop material 76 on the outside of first inner flap 64 to secure IV bag 12 in place. First and second inner flaps 64 and 66 thus comprise a girdle around the midsection of IV bag 12, to restrain it laterally against inner back 30.

A first outer flap 70 is also flexibly attached along the side of inner back 30, adjacent first inner flap 64. Similarly, a second outer flap 72 is flexibly attached along the opposite side of inner back 30. The first and second outer flaps are both longer and wider than first and second inner flaps 64 and 66. When folded over the IV bag after it is laterally secured by inner flaps 64 and 66, first and second outer flaps 70 and 72 overlap each other (and the inner flaps) and substantially cover and enclose IV bag 12.

Pouch 14 is attached to the outside surface of second outer flap 72 and the other surface of the second outer flap is covered with loop material 74. As shown in FIG. 3, two generally parallel strips of hook material 80 are applied to the outer surface of first outer flap 70 to couple with loop material 74, securing second outer flap 72 to first outer flap 70.

Prior to folding second outer flap 72 over first outer flap 70, top straps 50 and 52 are folded over first inner flap 64 and second inner flap 66. Top straps 50 and 52 pass between outlet port 20 and secondary port 24 and are folded over the inner flaps. Strips of hook material 56 on the top straps engage loop material 76 on the outer surface of second inner flap 66. The top straps thus secure IV bag 12 against longitudinal movement relative to inner back 30. In addition, loop material strap 62 is folded over outlet port 20 and is coupled to hook material 60, further securing this end of IV bag 12 to inner back 30. The extending portion of outer back 32 is folded over the open end of inner back 30, closing the opening through which plastic plate 40 was inserted.

Pouch 14 is sized to accommodate IV pump 16 and is provided with two closure straps 82 that are covered on their inner surface with hook material 84. Patches of loop material 86 are applied to the outer facing surface of pouch 14 to engage hook material 84, thereby securing closure straps 82 after IV pump 16 has been inserted into pouch 14 (see FIG. 4). An opening 88 is provided in pouch 14, giving the user access to controls on the left side of IV pump 16, and a window 90 is provided in the top surface of the pouch to enable the user to observe alphanumeric messages on a display 92 of the IV pump that is visible through the window.

FIG. 4 clearly shows how IV pump 16 is inserted into pouch 14 so that closure straps 82 can be closed over the side of the pump by latching hook material 84 with loop material 86. IV pump 16 is inserted into pouch 14 after supply line 18 is coupled to the pump, passing through a rotary peristaltic pumping mechanism 96, which is disposed on the right side of the pump. Fluid is forced through a fluid line 94 by the rotary peristaltic pumping mechanism, and the fluid line is coupled into the patient's body, e.g., through a catheter.

After IV pump 16 has been secured into pouch 14 by latching closure straps 82, supply line 18 is fastened to the second outer flap using a strap 98, the downwardly facing surface of which is covered with hook material; the hook material engages an underlying patch of loop material 100 attached to the outer surface of second flap 72.

In FIG. 5, pack 10 is shown with IV bag 12 and pump 16 secured in place. In this FIGURE, an exemplary carrying bag 110 is illustrated for enclosing pack 10 and transporting it while the medicinal fluid within IV bag 12 is infused into the patient. Carrying bag 110 represents only one example of a variety of different types of carrying bags in which pack 10 can be enclosed to facilitate the safe transport of IV pump 16 and IV bag 12.

In the example shown in FIG. 5, carrying bag 110 includes a back 112. Around the perimeter of back 112 is attached a side 114, comprising a strip of material sewn to stand upright relative to back 112. Similarly, a top 116 of carrying bag 110 includes a side 118 around its periphery that extends upright relative to the top. Side 118 is flexibly attached adjacent one end of top 116 to side 114. A linear sliding fastener, of the type commonly known by the trademark ZIPPER™ extends around the open edges of both side 114 and side 118, enabling the two sides to be connected together whenever sliders 120 and 122 are slid along the linear sliding fastener, engaging teeth (not shown) on each linear sliding fastener. Sliders 120 and 122 do not meet, since the linear sliding fastener terminates at a point 138 along the edges, leaving a gap of approximately one-half inch through which fluid line 94 extends from inside carrying bag 110 for supplying medicinal fluid to the patient.

A shoulder strap 126 is provided on carrying bag 110, and is coupled to one of two D rings 128 with a spring clip 130. D rings 128 are disposed at each end of a reinforcement strip 132 that is attached to the middle of side 114. Shoulder strap 126 includes a shoulder pad 134 for cushioning the weight of the pack, IV pump, and IV bag in carrying bag 110 when the assembly is carried by slinging shoulder strap 126 over the patient's shoulder.

Inside back 112 are disposed two patches 136 of the hook material. The underlying surface of outer back 32 is covered with loop material 78. Patches 136 of the hook material engage the loop material on outer back 32, stabilizing pack 10 within carrying bag 110. However, it will be appreciated that other techniques for securing pack 10 within a carrying bag can alternatively be implemented. Since pack 10 stabilizes IV bag 12 and pump 16 and maintains supply line 18 and fluid line 94 in a position that minimizes the opportunity for crimping the lines or restricting flow through the lines, pack 10 is ideally suited to be transported in a wide variety of sizes and styles of carrying bags, thereby enabling a patient to select a preferred carrying bag for IV pump 16 and IV bag 12. Optionally, carrying bag 110 may be sold with pack 10, since it is ideally sized for use with the pack. However, many other sizes, styles, and types of fabric could be used for the carrying bag in which pack 10 is transported while IV pump 16 is in use.

Although the present invention has been described in connection with the preferred form of practicing it, those of ordinary skill in the art will understand that many modifications can be made thereto within the scope of the claims that follow. Accordingly, it is not intended that the scope of the invention in any way be limited by the above description, but instead be determined entirely by reference to the claims that follow.

The invention in which an exclusive right is claimed is defined by the following:

1. A pack for transporting an ambulatory IV pump and an IV bag while a medicinal fluid in the IV bag is infused into a patient by the pump, comprising:

(a) a pack board sized to support the IV bag when one side of the IV bag is in contact with the pack board;

(b) a plurality of flaps and a plurality of straps connected to the pack board, securing the IV bag to the pack board both laterally and transversely; and (c) a pouch flexibly connected to the pack board and sized to hold the ambulatory IV pump, so that said pump may be coupled to the IV bag while said pump is disposed within said pouch.

2. The pack of claim 1, further comprising a hook material and a loop material disposed on the plurality of flaps and on the plurality of straps, for securing the IV bag to the pack board, said hook material engaging said loop material to couple the plurality of flaps in overlapping closure and to hold the plurality of said straps.

3. The pack of claim 1, wherein the plurality of flaps include two inner flaps that are flexibly connected to the pack board to encompass a middle portion of the IV bag, said inner flaps being connected together where the inner flaps overlap, to provide lateral support for the IV bag.

4. The pack of claim 3, wherein the plurality of straps include a strap that is flexibly connected to the pack board adjacent one end thereof, said strap overlapping the inner flaps and being connected thereto, to restrain one end of the IV bag.

5. The pack of claim 1, wherein the pack board comprises a pocket made of fabric and a plastic plate inserted within the pocket for providing rigidity to the pack board.

6. The pack of claim 1, wherein the plurality of straps include a strap that is flexibly connected to one end of the pack board so that the strap is adapted to pass through a hanger slot on an end of the IV bag and then to attach to the pack board to secure the IV bag to the pack board.

7. The pack of claim 1, wherein the plurality of flaps include two outer flaps flexibly connected to opposite sides of the pack board, said outer flaps overlapping and substantially covering the IV bag when folded over the IV bag, said pouch being disposed on an outer surface of the one of the outer flaps.

8. The pack of claim 1, wherein the pouch includes an opening for insertion of the ambulatory IV pump, and wherein the plurality of straps includes a strap for securing the ambulatory IV pump inside the pouch.

9. The pack of claim 1, wherein the plurality of straps includes a strap that is connected to the pack board adjacent one end thereof, said strap extending generally parallel to said one end of the pack board for transversely securing an outlet port of the IV bag to the pack board.

10. The pack of claim 1, further comprising a hanger loop disposed adjacent one end of the pack board.

11. The pack of claim 1, further comprising a carrying bag for enclosing and transporting the pack board, the plurality of flaps, the plurality of straps, the pouch, the IV bag secured on the pack board, and the ambulatory IV pump in the pouch.

12. The pack of claim 11, wherein the carrying bag includes a shoulder strap.

13. Apparatus enabling an ambulatory IV pump and a container of medicinal fluid to be transported while the medicinal fluid is infused into a patient's body, comprising:

(a) a rigidized back panel for supporting said container of medicinal fluid;

(b) a pair of inner flaps flexibly attached to the back panel and extending from opposite sides of said back panel, said inner flaps being sufficiently long so as to overlap when folded over the container of medicinal fluid, a patch of a hook material covering at least a portion of a surface of one inner flap, and a patch of a loop material covering at least a portion of an opposite surface of the other inner flap, said patch of hook material engaging said patch of loop material when the inner flaps are folded over and overlap, thereby securing the container of medicinal fluid laterally on the back panel;

(c) at least one strap connected adjacent one end of the back panel, said at least one strap being sufficiently long to overlap the inner flaps and including one of a strip of a hook material and a strip of a loop material on at least a portion of one surface of said at least one strap, said strip engaging one of the patches of the loop and hook material on one of the inner flaps to secure one end of the container of medicinal fluid;

(d) a hanger strap connected adjacent an opposite end of the back panel, said hanger strap being adapted to engage a hanger slot on the container of medicinal fluid and including a strip of one of a hook material and a loop material disposed on one surface of the hanger strap, said strip engaging a corresponding opposite one of a loop material and a hook material that is connected to a surface of the back panel to secure the container of medicinal fluid to said opposite end of the back panel; and (e) a pouch coupled to said back panel, said pouch being sized to hold said ambulatory IV pump during transport of the pump while the medicinal fluid is being infused, so that said pump may be coupled to the IV bag while said pump is disposed within said pouch.

14. The apparatus of claim 13, wherein the back panel comprises a pocket into which a plastic panel is inserted, said plastic panel being sized to substantially fill the pocket and increase the rigidity of said back panel.

15. The apparatus of claim 13, further comprising a first outer flap and a second outer flap, said first and second outer flaps being flexibly attached to opposite sides of the back panel and being sufficiently long to overlap when folded over the container of medicinal fluid secured by the inner flaps, an outer surface of the second outer flap being at least partially covered with one of a hook material and a loop material, and an inner surface of the first outer flap being at least partially covered with an opposite one of the hook material and the loop material on the second outer flap so that the first outer flap is secured to the second outer flap when first outer flap is folded over the second outer flap, said pouch being attached to an outer surface of said first outer flap.

16. The apparatus of claim 13, wherein said pouch has an opening for insertion of the ambulatory IV pump, further comprising at least one closure strap that extends across said opening to secure the pump within the pouch.

17. The apparatus of claim 13, further comprising a tie down strap disposed adjacent said one end of the back panel, said tie down strap extending generally parallel to said one end and being secured to the back panel to overlap an outlet port into the container of medicinal fluid to provide transverse support to an end of the container of medicinal fluid at which the outlet port is disposed.

18. The apparatus of claim 13, further comprising a hanger loop connected to said other end of the back panel, for carrying the apparatus and for hanging the apparatus.

19. The apparatus of claim 13, further comprising a carrying bag that includes a back section and a front section sized to enclose the container of medicinal fluid and the ambulatory IV pump, a portion of an edge of the back section being flexibly connected to a corresponding portion of an edge of the front section, a linear slide fastener extending around remaining portions of the edges of the front and back sections, for closing the carrying bag.

20. The apparatus of claim 19, further comprising a shoulder strap coupled to the carrying bag to facilitate its transport by the patient with the ambulatory IV pump and container of medicinal fluid secured and supported inside the carrying bag on the back panel.

* * * * *